US00PP30609P2

(12) United States Plant Patent
Van Swieten

(10) Patent No.: US PP30,609 P2
(45) Date of Patent: Jun. 25, 2019

(54) ***PHALAENOPSIS* ORCHID PLANT NAMED 'PHALFYTYO'**

(50) Latin Name: ***Phalaenopsis* hybrid**
Varietal Denomination: PHALFYTYO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/732,969

(22) Filed: Jan. 19, 2018

(51) Int. Cl.
*A01H 6/62* (2018.01)

(52) U.S. Cl.
USPC ..... Plt./311

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHALFYTYO', particularly characterized by having small, white flowers with a slightly red-purple center and unique red-purple lip, 1 to 3 peduncles that are short and sturdy, leaves that are oblong, and is propagated by meristem tissue culture, is disclosed.

3 Drawing Sheets

Genus and species: *Phalaenopsis* hybrid.
Variety denomination: 'PHALFYTYO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFYTYO'.

The new *Phalaenopsis* plant is a product of a planned breeding program conducted by the inventor in Bleiswijk, The Netherlands. The objective of this breeding program was to create a new short *Phalaenopsis* plant with attractive and small white flowers with a slightly red-purple center and unique red-purple lip, suitable for potted plant production.

The new *Phalaenopsis* plant 'PHALFYTYO' is a result of cross-pollination made by the inventor in August 2008 in Bleiswijk, The Netherlands of the proprietary female, or seed parent, *Phalaenopsis* hybrid '01-1789' (unpatented) with the proprietary male, or pollen parent, *Phalaenopsis* hybrid 'PHALDOMEO' (U.S. Plant Pat. No. 25,682).

The new *Phalaenopsis* was selected by the inventor as a single plant within the progeny of the stated cross-pollination in a controlled greenhouse in Bleiswijk, The Netherlands in August 2011. Asexual reproduction of the new *Phalaenopsis* plant by meristem tissue culture since 2013 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 25, 2017. 'PHALFYTYO' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALFYTYO' as a new and distinct variety of *Phalaenopsis* plant.

1) Small, white flowers with a slightly red-purple center and unique red-purple lip;
2) 1 to 3 peduncles;
3) Peduncle is short and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in November 2017. Colors in the photographs may differ from the color values cited in the detailed botanical description, which accurately describe the actual colors of the new variety.

DESCRIPTION OF THE NEW VARIETY

Figure 1:
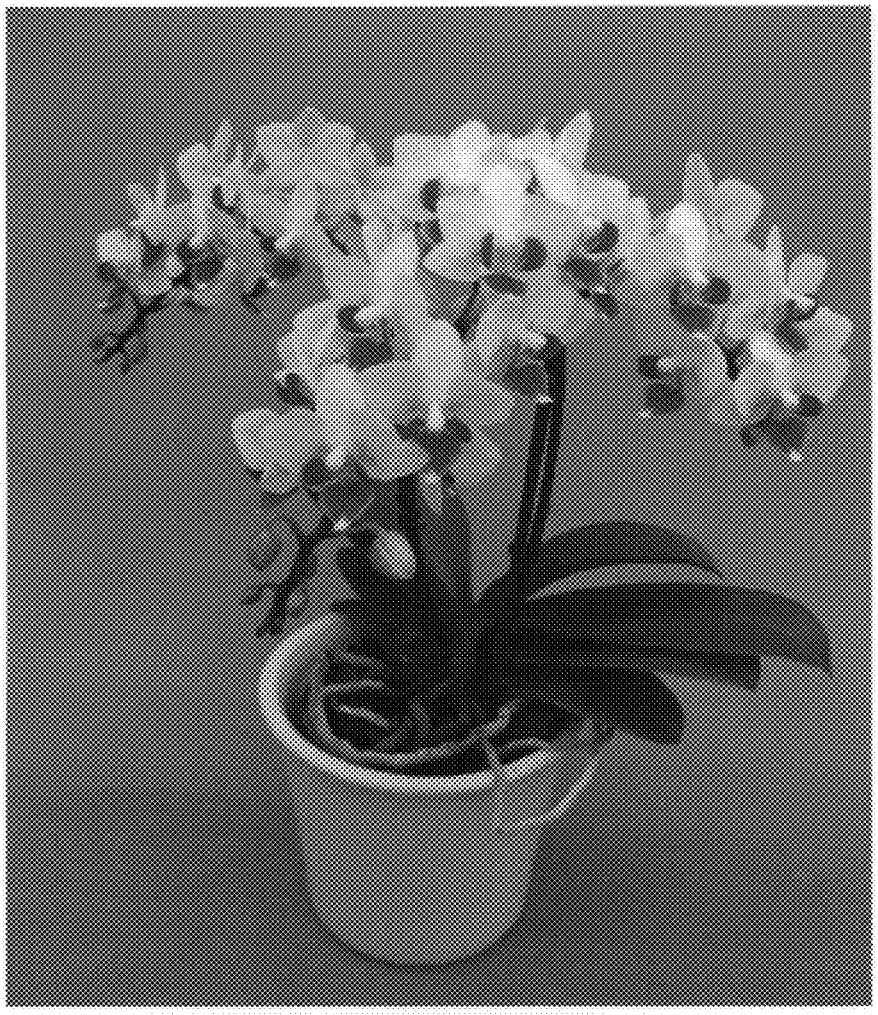
FIG. 1 shows the overall plant habit, including blooms, buds and foliage of 'PHALFYTYO'.
Figure 2:
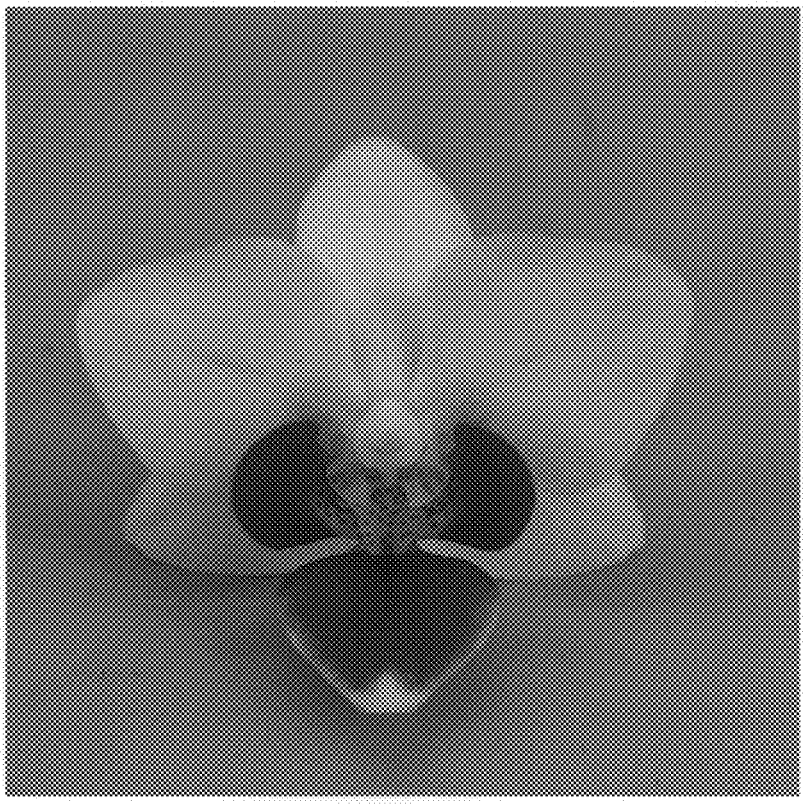
FIG. 2 shows a close-up of a flower of 'PHALFYTYO'.
Figure 3:
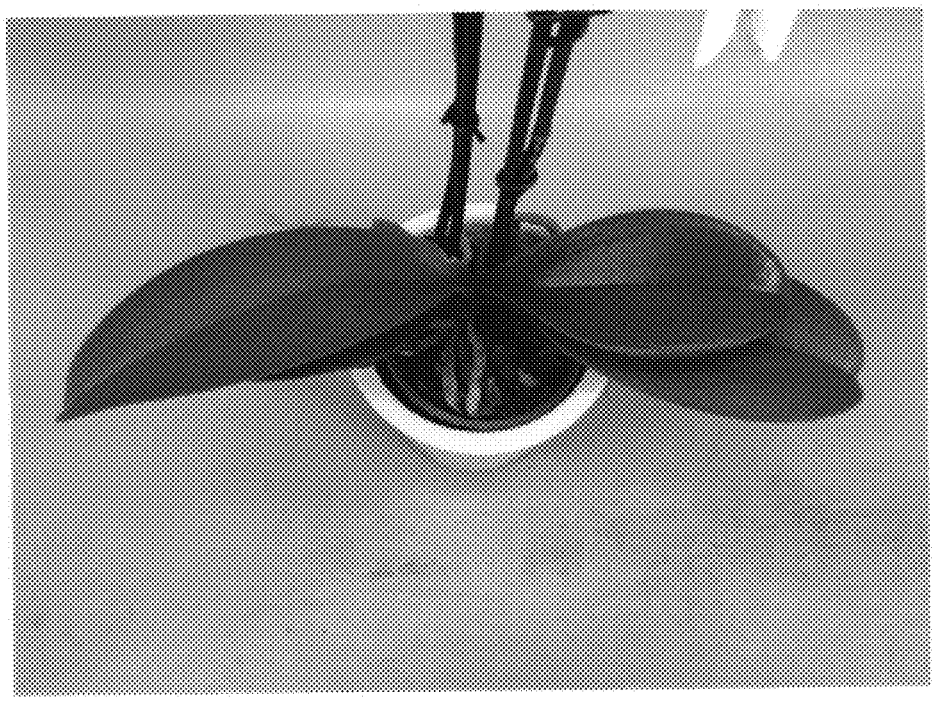
FIG. 3 shows an overhead view of the leaves of 'PHALFYTYO'.

The following detailed description sets forth the distinctive characteristics of 'PHALFYTYO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in November 2017 on flowering plants which were planted in 9 centimeter (diameter) pots. After in-vitro propagation, the plants were grown in nursery trays for 18-20 weeks, followed by transplantation to 9 centimeter (diameter) pots and grown in a greenhouse between 27° C. to 29° C. for 25 weeks, continued by a cooling period of 6 weeks between 18° C. to 20° C. and 11 weeks in a greenhouse of 21° C. Flowering occurs after 42-weeks in a 9 centimeter pot.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFYTYO'.

Parentage:

*Female parent*.—*Phalaenopsis* cultivar '01-1789' (unpatented).

*Male parent*.—*Phalaenopsis* cultivar 'PHALDOMEO' (U.S. Plant Pat. No. 25,682).

Propagation:

*Type*.—Meristem tissue culture.

Roots:

*Root description*.—Greyed-green colored roots (RHS 190B/C) with branching lateral roots having red-purple colored root tips (RHS N79B/C).

Plant:

*Commercial crop time to flowering*.—Following asexual propagation (in-vitro), the rooted cuttings grow for 18-20 weeks. After transplantation in 9 cm pots, the plants are finished after 40 to 42 weeks.

*Growth habit of peduncle*.—Standard, green leaves, raceme to panicle.

*Height (from soil level to top of inflorescence)*.—Approximately 20.0 cm to 25.0 cm.

*Width (measured from leaf tips)*.—About 27.0 cm to 29.0 cm.

*Vigor*.—Strong.

Leaves:

*Mature leaves*.—Quantity per plant: 7 to 9 leaves are produced before flowering. Length (fully expanded): 14.0 cm to 16.0 cm. Width: 6.0 cm to 7.0 cm. Shape: Oblong. Base shape: Moderately elongated. Apex: Acute unequal. Leaf blade angle with the petiole (measured from the horizontal position): Between 20 degrees and 35 degrees. Leaf margin: Entire. Color: Upper surface: RHS 144A/146A. Lower surface: RHS 146B. Variegation: Absent. Texture (upper surface): Rough. Thickness: 2.4 mm to 2.6 mm. Venation: Pattern: Parallel. Color of the midvein: Upper surface: RHS 146A. Lower surface: RHS 146B.

Peduncle:

*Quantity per plant*.—1 to 3.

*Number of flowers per peduncle*.—14 to 20.

*Length*.—20.0 cm to 25.0 cm.

*Diameter*.—3.8 mm to 4.3 mm.

*Strength*.—Moderate.

*Aspect*.—Upright to slightly pendant.

*Texture*.—Smooth.

*Color*.—Mix of brown (RHS 200B/C) with a touch of light green (RHS 195B).

*Internode length*.—2.5 cm to 3.5 cm.

*Callosities*.—None.

Inflorescence description:

*Appearance*.—Upright to slightly pendant, raceme to panicle inflorescence with bilaterally symmetrical flowers that open in succession beginning with the lowermost flower.

*Inflorescence size*.—Height (from base to tip): 100.0 mm to 130.0 mm.

*Number of inflorescences of the plant*.—There are 2 inflorescences present. One is panicle (branched, and this branch is raceme) and the other is raceme.

*Flowering time*.—First flowers can be expected 7 to 8 months after planting in a 9 cm (diameter) pot.

*Flower*.—Height: 34.0 mm to 36.0 mm. Diameter: 38.0 mm to 40.0 mm. Depth of lip: 13.0 mm to 15.0 mm.

*Flower longevity*.—On the plant: 8 to 12 weeks.

*Fragrance*.—Absent.

*Flower bud*.—Average size: Medium. Length: 14.0 mm to 16.0 mm. Width: 10.0 mm to 14.0 mm. Shape: Egg shaped. Color: Light green (RHS 145C/D) at the base and diluting light red-purple (RHS N78D).

*Petals*.—Arrangement: Open/free. Shape: Semi-circular. Apex: Obtuse asymmetric. Margin: Slightly undulated. Position of broadest part: Towards base. Length (from base to tip): 15.0 mm to 17.0 mm. Width: 16.0 mm to 18.0 mm. Color (when fully opened): Upper surface: Basic color: White (RHS NN155C). Over color: Light pink-purple (RHS N78C) at the base. Lower surface: Basic color: White (RHS NN155C). Over color: Light red-purple at the base and stripe in the middle (RHS N78D).

*Dorsal sepal*.—Shape: Elliptic. Apex: Slightly emarginated symmetric. Margin: Entire. Length (from base to tip): 18.0 mm to 20.0 mm. Width: 12.0 mm to 14.0 mm. Color (when fully opened): Upper surface: Basic color: White (RHS NN155C). Over color: Absent. Lower surface: Basic color: White (RHS NN155C). Over color: Light purple (RHS 76B).

*Lateral sepals*.—Shape: Ovate. Apex: Obtuse asymmetric. Margin: Entire. Length (from base to tip): 20.0 mm to 22.0 mm. Width: 13.0 mm to 15.0 mm. Color (when fully opened): Upper surface: Basic color: White (RHS NN155C). Over color: Few red-purple stripes (RHS N78B) at the base. Lower surface: Basic color: White (RHS NN155C). Over color: Light purple (RHS 76B).

*Labellum (lip)*.—Whiskers: Present. Length of whiskers: 1.0 mm to 2.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 13.0 mm to 15.0 mm. Width: 6.0 mm to 8.0 mm. Color: Yellow (RHS 3A) at the base with few red-purple (RHS 71A) stripes and spots; red-purple (RHS N78A) toward the margin.

*Apical lobe*.—Shape: Circular. Margin: Entire. Length: 13.0 mm to 15.0 mm. Width: 14.0 mm to 16.0 mm.

Color: Red-purple (RHS 71A) at the base; red-purple (RHS N78A) and white (RHS NN155C) toward the whiskers.

*Callus*.—Average size: Small. Height: 3.0 mm to 4.0 mm. Length: 4.0 mm to 5.0 mm. Width: 3.0 mm to 4.0 mm. Color: Yellow (RHS 9B), dotted (RHS 60A).

Reproductive organs:

*Column*.—Length: 7.0 mm to 9.0 mm. Diameter: 4.2 mm to 4.4 mm. Color: White (RHS NN155C).

*Pollinia*.—Quantity: 2. Diameter: 0.7 mm to 0.8 mm. Color: Orange (RHS 25A).

*Ovary*.—Length: 7.0 mm to 9.0 mm. Diameter: 1.8 mm to 2.0 mm.

*Pedicel*.—Length: 23.0 mm to 25.0 mm. Diameter: 2.1 mm to 2.3 mm. Color: Diluting dark red (RHS 187B) and light green (RHS 195B) at the base; white (RHS N155B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent of 'PHALFYTYO', cultivar '01-1789' (unpatented), is no longer in existence, so a meaningful comparison cannot be made.

'PHALFYTYO' differs from male parent plant 'PHALDOMEO' (U.S. Plant Pat. No. 25,682) in that 'PHALFYTYO' has white flowers, a white column and a slightly emarginated dorsal sepal apex, whereas 'PHALDOMEO' has purple flowers, a purple column and an obtuse dorsal sepal apex.

'PHALFYTYO' is most similar to the commercial *Phalaenopsis* plants named 'PHALCRYL' (unpatented) and 'PHALELENO' (unpatented). 'PHALFYTYO' differs from the commercial variety 'PHALCRYL' in that 'PHALFYTYO' has a weakly spatulate lateral lobe shape, whereas 'PHALCRYL' has a spatulate lateral lobe shape. Additionally, 'PHALFYTYO' has smaller flowers and a shorter plant length (excluding pot) than 'PHALCRYL'.

'PHALFYTYO' differs from the commercial variety 'PHALELENO' in that 'PHALFYTYO' has a weakly spatulate lateral lobe shape, whereas 'PHALELENO' has a spatulate lateral lobe shape. Additionally, 'PHALFYTYO' has smaller flowers and a shorter plant length (excluding pot) than 'PHALELENO'.

I claim:

1. A new and distinct variety of *Phalaenopsis* plant named 'PHALFYTYO', substantially as described and illustrated herein.

* * * * *